(12) United States Patent
Asselineau et al.

(10) Patent No.: US 7,192,719 B2
(45) Date of Patent: Mar. 20, 2007

(54) ANTIBODIES SPECIFIC FOR PAPILLARY FIBROBLASTS AS MARKERS FOR SKIN QUALITY

(75) Inventors: Daniel Asselineau, Antony (FR); Arnold Caplan, Cleveland, OH (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/619,188

(22) Filed: Jul. 15, 2003

(65) Prior Publication Data
US 2004/0082016 A1 Apr. 29, 2004

Related U.S. Application Data

(63) Continuation of application No. 09/725,269, filed on Nov. 29, 2000, now abandoned.

(30) Foreign Application Priority Data
Dec. 3, 1999 (FR) .................... 99 15292

(51) Int. Cl.
*G01N 33/53* (2006.01)
(52) U.S. Cl. .................... 435/7.1; 435/7.2; 435/7.92; 435/971; 435/40.5; 530/388.22
(58) Field of Classification Search ............... 435/7.1, 435/7.2, 7.92, 971, 40.5; 530/387.2, 388.2
See application file for complete search history.

(56) References Cited

OTHER PUBLICATIONS

Histochemical J. 1999 vol. 31, p. 549-558.*
Sorrell et al., "A Monoclonal Antibody which Recognizes a Glycosaminoglycan Epitope in both Dermatan Sulfate and Chondroitin Sulfate Proteoglycans of Human Skin", The Histochemical Journal, 31: 549-558, 1999.
Sorrell et al., "Identification of Monclonial Antibodies that Recognize Novel Epitopes in Native Chondroitin/Dermatan Sulfate Glycosaminoglycan Chains: Their Use in Mapping Functionally Distinct Domains of Human Skin", The Journal of Histochemistry and Cytochemistry, vol. 38, No. 3, pp. 393-402, 1990.
Schönherr et al., "Difference in Decorin Expression by Papillary and Reticular Fibroblasts *in vivo* and *in vitro*", Biochem J. (1993) 290, 893-899.
Hunzelmann et al., "Altered Immunohistochemical Expression of Small Proteoglycans in the Tumor Tissue and Stroma of Basal Cell Carcinoma", The Journal of Investigative Dermatology, vol. 104, No. 4, pp. 509-513, 1995.
Willen et al., "Patterns of Glycosaminoglycan/Proteoglycan Immunostaining in Human Skin During Aging", The Journal of Investigative Dermatology, vol. 96, No. 6, pp. 968-974, 1991.
Haschisuka et al., "Proteoglycans in Albo-Papuloid Lesions of the Pasini Form of Dominant Dystrophic Epidermolysis Bullosa", The Kurume Medical Journal, vol. 42, pp. 1-8, 1995.
Asselineau et al., "Complex Reconstructed Skin Equivalents Made with Papillary and Reticular Fibroblasts Populations Incorporated in Distinct Layers: Re-expression of Papillary and Reticular Fibroblast Characteristics after Grafting onto Nude Mice".
Asselineau et al., "Human Epidermis Reconstructed by Culture: Is It Normal?", The Journal of Investigative Dermatology, vol. 86, No. 2, pp. 181-186, 1986.
Hollinshead, W. Henry et al., "The Skin and Its Appendages." Textbook of Anatomy, $4^{TH}$ Edi., Chapter 10, Harper & Row, Publishers, Philadelphia, 1985, pp. 139-141.
Wheater, P.R., et al., "Fig. 9.6 Skin Appendages." Functional Histology: A Text and Color Atlas, $2^{nd}$ Ed., Churchill Livingstone, Edinburg, 1987, p. 134.

* cited by examiner

*Primary Examiner*—Mary E. Ceperley
*Assistant Examiner*—Jacob Cheu
(74) *Attorney, Agent, or Firm*—Buchanan Ingersoll, P.C.

(57) ABSTRACT

Whether or not a sample of skin or of a skin equivalent contains such amount of a papillary fibroblast population as to be considered a normal skin is determined by labelling said skin or skin equivalent with at least one antibody specific for papillary fibroblasts and evaluating the extent of such labelling as a marker for skin or skin equivalent quality.

7 Claims, 1 Drawing Sheet

ANTIBODIES SPECIFIC FOR PAPILLARY FIBROBLASTS AS MARKERS FOR SKIN QUALITY

CROSS-REFERENCE TO PRIORITY APPLICATION

This application is a continuation of application Ser. No. 09/725,269, filed on Nov. 29, 2000 now abandoned.

This application claims priority under 35 U.S.C. § 119 of FR-99/15292, filed Dec. 3, 1999, hereby expressly incorporated by reference.

BACKGROUND OF THE INVENTION

1. Technical Field of the Invention

The present invention relates to the use of at least one antibody specific for papillary fibroblasts as a marker for the quality of skin, in particular of a skin equivalent.

2. Description of the Prior Art

It is of course well known that human skin consists of two closely linked compartments or strata, namely, the epidermis and the dermis.

The epidermis is principally comprised of three cell types, keratinocytes, which themselves constitute the majority of the cells of the epidermis, melanocytes and Langerhans cells. These cells constitute a keratinized epithelium which is differentiated into superposed layers or strata surmounted by a layer of dead cells forming the stratum corneum.

The dermis provides the epidermis with a solid support. It is also the nourishing element of the epidermis. It principally comprises fibroblasts and an extracellular matrix which is itself principally collagen, elastin and a substance known as "ground substance". This set of extracellular components is synthesized by the fibroblasts. Leukocytes, mastocytes and tissue macrophages also are present therein. Too, it also comprises blood vessels and nerve fibers. In normal skin, i.e., skin which is neither pathological nor cicatricial, the fibroblasts are in the quiescent state, i.e., non-proliferative, relatively inactive in metabolic terms and immobile.

Indeed, the dermis is subdivided into two regions; firstly, a thin superficial dermis, termed papillary dermis, and secondly, the deep dermis, termed reticular dermis, which constitutes the great majority of the dermis.

The papillary dermis is the part of the dermis which is in contact with the epidermis, and it contains so-called papillary fibroblasts.

The reticular dermis is the region of the dermis which then extends down to the subcutaneous fatty layer, and it contains the reticular fibroblasts. In normal skin, these two regions reflect significant differences. The papillary dermis is metabolically more active than the reticular dermis.

Papillary and reticular fibroblasts in culture exhibit differences in their growth potential. With immunolabelling, it is possible to demonstrate that decorin, small-sized dermatan sulfate proteoglycan (DSPG), is more abundant in the papillary dermis than in the reticular dermis. Papillary fibroblasts secrete up to approximately 6 times more decorin than reticular fibroblasts.

Thus, in normal skin, the dermis comprises of at least two fibroblast populations, which can only have fundamental consequences on the skin itself.

In the domain of skin equivalents (or skin reconstructed in vitro), it is known to prepare dermis equivalents with each of the fibroblast populations isolated beforehand. It is also known to prepare dermis equivalents into which the two populations isolated beforehand are introduced. However, the problem remains of identifying the various fibroblast populations in dermis equivalents reconstructed from a random population of fibroblasts. After establishing in culture the dermis equivalent, does the latter have at least the two fibroblast populations, reticular and papillary, which are present in the dermis of normal skin? Now, it was previously recognized that normal skin has these two populations, and it is understood that skin reconstructed in vitro will be all the more similar to normal skin when it includes at least the two fibroblast populations.

To date, to applicants' knowledge, there exists no simple and effective means, particularly a means which does not impair the skin equivalent, which makes it possible to establish without ambiguity whether reconstructed skin either does or does not contain at least the two papillary and reticular fibroblast populations.

SUMMARY OF THE INVENTION

It has now surprisingly and unexpectedly been determined that papillary fibroblasts express a specific epitope which is not present, or present in only fractional amounts, in reticular fibroblasts. Thus, the present invention features utilization of antibodies, in particular monoclonal antibodies, specific for this epitope, to label this particular population of dermal fibroblasts. Accordingly, using this antibody, it can be determined whether a skin equivalent has the two papillary and reticular fibroblast populations.

Too, this invention features the use of at least one antibody specific for papillary fibroblasts as a marker for the quality of skin, particularly of a skin equivalent.

BRIEF DESCRIPTION OF THE DRAWING

The FIGURE of Drawing is a photomicrograph of a section of normal human skin immunolabelled with the PG4 mouse monoclonal antibody.

DETAILED DESCRIPTION OF BEST MODE AND SPECIFIC/PREFERRED EMBODIMENTS OF THE INVENTION

Figure 1:
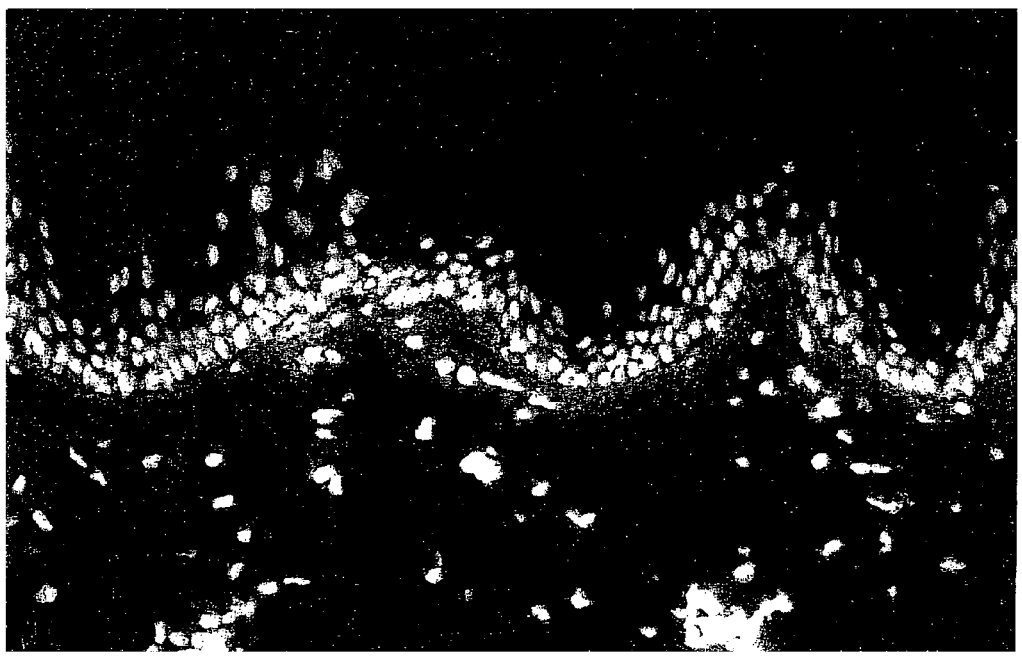

More particularly, according to the present invention, by the expression "marker for the quality" is intended any marker which effectively indicates the presence in skin or in a skin equivalent of a biological element which is present in normal skin.

Consistent herewith, by the term "marker" is intended any element for which the presence, the absence, the modification of expression or the modification of distribution can be measured. Exemplary markers include epitopes, nucleic acids (ribonucleic or deoxyribonucleic acid), antibodies, proteins or a group of proteins which may or may not be linked, ions, cellular organelles, lipids or polysaccharides. According to this invention, the marker is an antibody.

The antibody can be a polyclonal or monoclonal antibody. Preferably, the antibody is monoclonal.

The antibody can be an antibody originating from any origin, i.e., derived from any animal such as, for example, horses, goats, mice, rats or rabbits. Preferably, the antibody is a mouse antibody. Even more preferably, the antibody is a mouse monoclonal antibody.

A preferred antibody according to the invention is the antibody referred to under the designation PG4, described in the publication by Sorrell et al. (*The Histochemical Journal*, 31, 549–558, 1999). This mouse monoclonal antibody is described as recognizing in skin at least one epitope specific for glycosaminoglycans, and particularly described as an anti-chondroitin sulfate (CS) and anti-dermatan sulfate (DS) monoclonal antibody. To date, this antibody has not been described as being specific for a particular population of dermal fibroblasts, namely, papillary fibroblasts.

Thus, the present invention features the use of the PG4 monoclonal antibody as a marker for papillary fibroblasts, particularly for papillary fibroblasts of skin, very particularly papillary fibroblasts of the dermis.

This invention also features the use of the PG4 monoclonal antibody as a marker for the quality of skin, particularly of skin equivalents, in particular of dermis equivalents obtained in vitro.

Any immunological labelling technique which employs at least one known antibody of the prior art can be used to carry out the labelling with the antibodies of the invention. In this respect, representative is the method described by Asselineau et al. (*J. I. D.*, 86, 181–186, 1986), or, alternatively, by Sorrell et al. (*The Histochemical Journal*, 31, 549–558, 1999).

The present invention thus also features a method for determining the quality of skin, particularly of a skin equivalent obtained in vitro, comprising carrying out immunological labelling on the skin and/or the skin equivalent employing at least one antibody specific for papillary fibroblasts, particularly the PG4 antibody.

The accompanying FIGURE of Drawing illustrates the invention more clearly, without limiting the scope thereof. In this FIGURE, the photograph is of a section of normal human skin after immunolabelling performed by indirect immunofluorescence using the PG4 monoclonal antibody, with propidium iodide counterstaining of the cell nuclei. The presence of intense labelling (light grey zone) of the upper dermis at the level of the epidermis (recognizable by the many cell nuclei labelled with propidium iodide) is noted, demonstrating the presence in this zone of papillary fibroblasts which express the epitope recognized specifically by the PG4 monoclonal antibody.

In order to further illustrate the present invention and the advantages thereof, the following specific example is given, it being understood that same is intended only as illustrative and in nowise limitative.

EXAMPLE

Immunological Labelling of Papillary Fibroblasts in Normal Skin:

Samples of normal skin derived from plastic surgery were embedded in Tissue-Tek, frozen in liquid nitrogen and stored in a freezer at −80° C. 4-micron-thick sections were prepared on a cryostat according to standard techniques. Labelling was performed using a conventional indirect immunofluorescence labelling technique (see Asselineau et al., *J. I. D.*, 86, 181–186, 1986) with 20 ml per section of the PG4 monoclonal antibody in pure state (culture supernatant) (see Sorrell et al., *The Histochemical Journal*. 31 549–558, 1999). 20 ml per section of an antibody directed towards mouse antibodies (mouse conjugate), obtained from the company Dako, were then placed on the sections and the sections were incubated according to the manufacturer's recommendation. After rinsing, the sections were contacted with a solution of PBS containing 0.5% propidium iodide, and then rinsed with PBS and mounted for observation under a fluorescence microscope, in order to stain the cell nuclei.

The presence of intense labelling of the dermis at the level of the epidermis was noted, demonstrating the presence in this zone of papillary fibroblasts expressing the epitope recognized specifically by the PG4 monoclonal antibody.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

Mouse hybridoma cells that produce the PG4 monoclonal antibody have been deposited in the American Type Culture Collection (ATCC), 10801 University Blvd., Manassas, Va., 20110-2209, USA on Mar. 28, 2006 under the terms of the Budapest Treaty on the International Recognition of the Deposit of Microorganism for the Purpose of Patent Procedure and have been given accession No. PTA-7447.

What is claimed is:

1. A regime for determining whether a sample of skin or of a skin equivalent contains a papillary fibroblast population as a marker that indicates normal skin comprising the steps of:
    (a) labeling the skin or skin equivalent with at least one antibody specific for papillary fibroblasts, and wherein the at least one antibody specific for papillary fibroblasts includes a PG4 monoclonal antibody; and
    (b) determining whether the skin or skin equivalent binds said antibody, wherein said binding indicates normal skin.

2. The regime of claim 1, wherein the labeling is present at the upper dermis at the level of the epidermis.

3. A regime for determining the presence of papillary fibroblasts in a sample comprising:
    (a) labeling said sample with at least one antibody specific for papillary fibroblasts, and wherein the at least one antibody comprises a PG4 monoclonal antibody; and
    (b) determining presence of bound antibody as a marker for the presence of said papillary fibroblasts.

4. The regime of claim 3, wherein the sample is a skin or skin equivalent sample.

5. The regime of claim 4, wherein the labeling is present at the upper dermis at the level of the epidermis in the skin or skin equivalent sample.

6. A regime for determining whether a sample of skin or of a skin equivalent contains a papillary fibroblast population comprising the steps of:
    (a) labeling the skin or skin equivalent with at least one antibody specific for papillary fibroblasts, and wherein the at least one antibody specific for papillary fibroblasts includes a PG4 monoclonal antibody; and
    (b) determining whether the skin or skin equivalent binds said antibody, wherein said binding indicates a papillary fibroblast population.

7. The regime of claim 6, wherein the labeling is present at the upper dermis at the level of the epidermis.

* * * * *